United States Patent [19]

Shiokawa et al.

[11] Patent Number: 4,670,599

[45] Date of Patent: Jun. 2, 1987

[54] 2,2-DICHLORO-3,3-DIMETHYLCYCLOPROPYLMETHYLAMINE

[75] Inventors: Kozo Shiokawa, Kawasaki; Shinzo Kagabu, Hachioji; Shinji Sakawa, Hino, all of Japan

[73] Assignee: Nihon Tokushu Noyaku Seizo K.K., Tokyo, Japan

[21] Appl. No.: 653,663

[22] Filed: Sep. 21, 1984

[30] Foreign Application Priority Data

Sep. 26, 1983 [JP] Japan .................................. 58-176508

[51] Int. Cl.$^4$ ............................................ C07C 87/32
[52] U.S. Cl. ...................................... 564/445; 564/455
[58] Field of Search ................................ 564/445, 455

[56] References Cited

U.S. PATENT DOCUMENTS 3,848,031 11/1974 Kishino et al. ...................... 260/956
4,220,770 9/1980 Gass ..................................... 544/208

FOREIGN PATENT DOCUMENTS 2219710 11/1972 Fed. Rep. of Germany .

OTHER PUBLICATIONS

Santelli, C., "Reactivite des Gem-Dibromecyclopropanes", *Tetrahedron Letters*, vol. 21, pp. 2893-2896 (1980).

*Primary Examiner*—Charles F. Warren
*Assistant Examiner*—John A. Sopp
*Attorney, Agent, or Firm*—Sprung, Horn, Kramer & Woods

[57] ABSTRACT

This invention relates to 2,2-dichloro-3,3-dimethylcyclopropylmethylamine, a novel compound which is useful as an agricultural and horticultural fungicide or as a synthetic intermediate for other cyclopropyl derivatives and other compounds, and to a process for production thereof.

1 Claim, No Drawings

2,2-DICHLORO-3,3-DIMETHYLCYCLOPROPYLMETHYLAMINE

DETAILED DESCRIPTION OF THE INVENTION

This invention relates to 2,2-dichloro-3,3-dimethylcyclopropylmethylamine, a novel compound which is useful as an agricultural and horticultural fungicide or as a synthetic intermediate for other cyclopropyl derivatives and other compounds, and to a process for production thereof.

More specifically, this invention relates to 2,2-dichloro-3,3-dimethylcyclopropylmethylamine represented by the following formula (I)

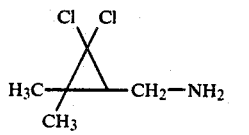

The compound of formula (I) in accordance with this invention can be produced, for example, by the following process to which the invention also pertains.

A process for producing 2,2-dichloro-3,3-dimethylcyclopropylmethylamine, which comprises reacting a compound represented by the following formula

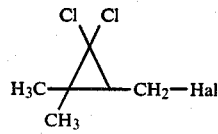

wherein Hal represents a halogen atom, with ammonia.

Investigations of the present inventors have shown that the above 2,2-dichloro-3,3-dimethylcyclopropylmethylamine not described in the known literature can be synthesized and that this compound is useful as an intermediate for the production of novel compounds having biological activities as an agricultural chemical, specifically for example an activity of controlling rice blast, such as N-2,2-dichloro-3,3-dimethylcyclopropylmethylphenylacetamide and N-2,2-dichloro-3,3-dimethylcyclopropylmethylbenzamide.

It has also been found that the compound of this invention is not only useful as an intermediate for producing other cyclopropyl derivatives such as exemplified above, but also by itself exhibits an excellent control effect against rice blast.

It is an object of this invention therefore to provide 2,2-dichloro-3,3-dimethylcyclopropylmethylamine, a novel compound, and a process for its production.

The compound of this invention can be produced, for example, by the following process.

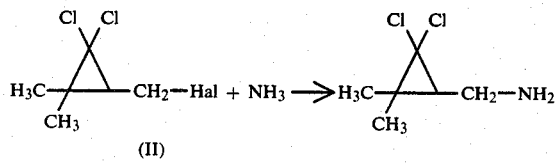

wherein Hal represents a halogen atom.

In the above reaction scheme, Hal specifically represents a halogen atom such as fluoro, chloro, bromo and iodo, preferably chloro and bromo.

In the process for producing the compound of this invention shown by the above reaction scheme, specific examples of the starting compound of formula (II) are 2,2-dichloro-3,3-dimethylcyclopropylmethyl chloride and 2,2-dichloro-3,3-dimethylcyclopropylmethyl bromide.

By citing a typical example, the process of this invention will be described specifically.

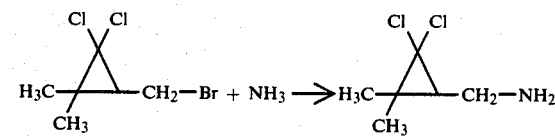

Desirably, the process for producing the above compound of this invention can be carried out by using a solvent or diluent. For this purpose, all inert solvents and diluents can be used.

Examples of such solvents or diluents include water; aliphatic, alicyclic and aromatic hydrocarbons (optionally chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above reaction can be carried out in the presence of an acid binder. Examples of the acid binder include the hydroxides, carbonates, bicarbonates and alcoholates of alkali metals which are generally used, and tertiary amines such as triethylamine, diethylaniline and pyridine.

The process of this invention can be carried out over a broad temperature range. Generally, it can be performed at a temperature between about −20° C. to the boiling point of the mixture, preferably between about 0° and about 100° C. Desirably, the reaction is carried out under atmospheric pressure, but it is also possible to operate under elevated or reduced pressures.

The following examples illustrate the present invention specifically. It should be noted however that the invention is not limited to these examples alone.

EXAMPLE 1

(synthesis example)

2,2-Dichloro-3,3-dimethylcyclopropylmethyl bromide (75 g) was dissolved in ethanol (200 ml), and 28% aqueous ammonia [NH$_4$OH] (70 g) was added. The mixture was heated in a sealed tube at 90° to 100° C. and 40 atomospheres for 20 hours. The reaction mixture was cooled, and the excess of ammonia gas was removed. Then, the mixture was poured into hexane (1 liter). The organic layer was washed with three 200 ml portions of water and dried. Hexane was evaporated and the remaining liquid was distilled to give 50 g of the desired compound of the invention, 2,2-dichloro-3,3-dimethylcyclopropylmethylamine with the boiling point 101°–103° C./20 mmHg.

The following Referential Example illustrates the synthesis of a novel biologically active compound produced from the compound of the invention as an intermediate.

REFERENTIAL EXAMPLE 2,2-Dichloro-3,3-dimethylcyclopropylmethylamine (3.34 g) and pyridine (2.0 g) were dissolved in toluene (30 ml), and under ice cooling, a solution of chloroacetyl chloride (2.24 g) in 20 ml of toluene was added dropwise. The mixture was stirred for 5 hours, and the reaction mixture was poured into water. The toluene layer was washed with a 3% aqueous hydrochloric acid solution twice, a saturated aqueous solution of sodium bicarbonate twice and then with water, and dried. Toluene was evaporated under reduced pressure, and the residue was washed with hexane to give 4.85 g of 2,2-dichloro-3,3-dimethylcyclopropylmethyl-chloroacetylamide with a melting point of 66° C.

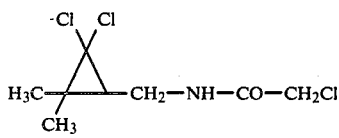 (D-1)

By the corresponding method the following biologically active compounds were synthesized.

| Compound No. | |
| --- | --- |
| D-2 (derivative) | Cl Cl \ / H₃C—△—CH₂—NH—CO—C₆H₅ CH₃ (mp. 96° C.) |
| D-3 (derivative) | Cl Cl \ / H₃C—△—CH₂—NH—CO—CH₂—C₆H₅ CH₃ (mp. 75° C.) |
| D-4 (derivative) | Cl Cl \ / H₃C—△—CH₂—NH—CO—CH₃ CH₃ (bp. 148–149° C./0.5 mmHg) |

BIOLOGICAL TEST EXAMPLE

Test on efficacy against rice blast by water surface application:

Preparation of a test compound:
Active compound: 50 parts by weight
Carrier: 45 parts by weight of a 1:5 mixture of diatomaceous earth and kaolin
Emulsifier: 5 parts by weight of polyoxyethylene alkylphenyl ether The active compound, the carrier and the emulsifier in the aforesaid amounts were pulverized and mixed to form a wettable powder. A predetermined amount of the wettable powder was diluted with water to prepare the test compound.

Testing method:

Rice plants (variety: Asahi) were grown in flooded porcelain pots having a diameter of 12 cm, three stocks per pot. In the early tillering stage of the rice plants, the test compound of a predetermined concentration prepared as above was poured by a pipette onto the water surface in the indicated dosages so that it did not directly contact the terrestrial parts of the rice plants. Four days later, a suspension of spores of rice blast fungus (*Pyricularia oryzae*) was sprayed onto the rice plants to inoculate the fungus. The plants were maintained for 24 hours in an incubator kept at a temperature of 23° to 25° C. and a relative humidity of 100. Thereafter, they were transferred to a glass greenhouse kept at a temperature of 20° to 28° C. Seven days after the inoculation, the plants were examined and rated on the following standards. The control index (%) was calculated.

| Degree of disease | Area of lesions (%) |
| --- | --- |
| 0 | 0 |
| 0.5 | 2 or less |
| 1 | 3–5 |
| 2 | 6–10 |
| 3 | 11–20 |
| 4 | 21–40 |
| 5 | 41 or more |

$$\text{Control index (\%)} = \frac{\left(\begin{array}{c}\text{Degree of disease}\\\text{of a non-treated lot}\end{array}\right) - \left(\begin{array}{c}\text{Degree of disease of}\\\text{a treated lot}\end{array}\right)}{\left(\begin{array}{c}\text{Degree of disease}\\\text{of the non-treated lot}\end{array}\right)} \times 100$$

The results are shown in Table 1. These results were obtained from three pots per lot.

TABLE 1

| Compound No. | Concentration of the active ingredient (g/m²) | Control index (%) | Phytotoxicity |
| --- | --- | --- | --- |
| Compound of the invention | 0.2 | 100 | — |
| D-1 | 0.8 | 100 | — |
| D-2 | 0.8 | 100 | — |
| D-3 | 0.8 | 100 | — |
| D-4 | 0.8 | 100 | — |

Note
(1) Compound of the invention

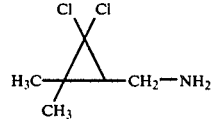

(2) D-1, D-2, D-3 and D-4 are the same as indicated hereinabove.
(3) The mark "—" in the column of phytotoxicity shows that there was no phytotoxicity.

It will be understood that the specification and examples are illustrative but not limitative of the present invention and that other embodiments within the spirit and scope of the invention will suggest themselves to those skilled in the art.

We claim:

1. 2,2-Dichloro-3,3-dimethyl-cyclopropylmethylamine of the formula

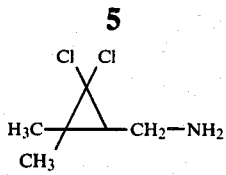
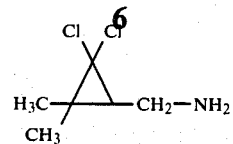
* * * * *

UNITED STATES PATENT AND TRADEMARK OFFICE
CERTIFICATE OF CORRECTION

PATENT NO. : 4,670,599

DATED : June 2, 1987

INVENTOR(S) : Kozo Shiokawa, et al.

It is certified that error appears in the above-identified patent and that said Letters Patent is hereby corrected as shown below:

Col. 6, lines 1-5          Delete entirely

Signed and Sealed this

First Day of March, 1988

Attest:

DONALD J. QUIGG

*Attesting Officer*      *Commissioner of Patents and Trademarks*